(12) United States Patent
Domae et al.

(10) Patent No.: US 6,234,176 B1
(45) Date of Patent: May 22, 2001

(54) DATA LOGGER FOR TRANSPORTABLE LIFE SUPPORT SYSTEM

(75) Inventors: Terrance Paul Domae, Cerritor; Donald Hanks, Woodland Hills; Stephen Francis Jenks, Redondo Beach, all of CA (US)

(73) Assignee: Integrated Medical Systems, Inc., Greenwich, CT (US)

( * ) Notice: Subject to any disclaimer, the term of this patent is extended or adjusted under 35 U.S.C. 154(b) by 0 days.

(21) Appl. No.: 09/286,111

(22) Filed: Apr. 2, 1999

Related U.S. Application Data

(63) Continuation-in-part of application No. 08/667,693, filed on Jun. 21, 1996, now Pat. No. 5,975,081.

(51) Int. Cl.$^7$ .................................................. A61B 19/00
(52) U.S. Cl. ........................................... 128/897; 128/845
(58) Field of Search .................................. 128/845, 846, 128/869, 870, 897; 5/624, 625, 628; 361/50; 600/21, 22

(56) References Cited

U.S. PATENT DOCUMENTS

| | | | |
|---|---|---|---|
| 5,398,149 | * | 3/1995 | Weil ........................................ 361/50 |
| 5,626,151 | * | 5/1997 | Linden .................................. 128/897 |

FOREIGN PATENT DOCUMENTS

WO 96 03955 * 7/1995 (WO).

* cited by examiner

*Primary Examiner*—Michael A. Brown
(74) *Attorney, Agent, or Firm*—Stetina Brunda Garred & Brucker

(57) ABSTRACT

A method for logging information representative of the operation of medical devices such as those of a transportable life support system includes communicating information from a plurality of medical devices to a storage device via at least one isolation circuit. The isolation circuit(s) mitigate interference with the medical devices so as to facilitate such data logging without adversely affecting the operation of the medical devices.

14 Claims, 4 Drawing Sheets

DATA LOGGER FOR TRANSPORTABLE LIFE SUPPORT SYSTEM

RELATED APPLICATION

This patent application is a continuation-in-part patent application of U.S. Ser. No. 08/667,693, filed Jun. 21, 1996, now U.S. Pat. No. 5,975,081 and entitled SELF-CONTAINED TRANSPORTABLE LIFE SUPPORT SYSTEM, the contents of which are hereby incorporated by reference.

FIELD OF THE INVENTION

The present invention relates generally to medical devices utilized to treat intensive care patients and more particularly to a data logger for a self-contained transportable life support system such as those which are utilized in the resuscitation, stabilization, and transport of medical patients. The data logger of the present invention interfaces to the medical devices of the transportable life support system in a manner which does not substantially interfere with the operation thereof, thereby attempting to maintain prior governmental clearance, such as Food and Drug Administration (FDA) clearance of medical devices in the United States.

BACKGROUND OF THE INVENTION

The need to transport medical patients and persons suffering from various medical emergency conditions such as heart attacks, strokes, etc. is well-known. Medical personnel speak of a "golden hour" within which such a medical patient must be transported to a medical facility so that proper medical care can be provided therefor. The survival rate for such medical patients is greatly enhanced if they are transported to the medical facility within the golden hour.

However, as those skilled in the art will appreciate, it is often difficult to transport a patient to a remotely located medical facility in a timely manner, particularly within the golden hour. Frequently accidents occur at remote locations and thus a substantial amount of time is required to transport the medical patient to a distant hospital. Also, in battlefield situations it is frequently impossible to transport a casualty immediately. In either instance, the patient may be located hundreds, if not thousands, of miles from a hospital, thus necessitating several hours of transport time. As such, it is frequently beneficial to perform various emergency medical procedures at the site of the medical problem, and then to attempt to provide ongoing medical care during transport to a remote hospital. The mortality rate of such transported medical patients is substantially reduced.

It is well-known to use various different medical devices in the field, i.e., at locations remote from a medical facility, so as to enhance a medical patient's chance of survival. For example, it is well-known to use an ECG and a defibrillator upon heart attack victims so as to monitor the condition thereof and so as to provide medical treatment therefor in field.

Typically, the medical patient is placed upon a stretcher and then various different medical devices are used upon the patient, as necessary. During transport the medical devices may either be temporarily disconnected from the patient, or alternatively may be hand carried along therewith by additional personnel. However, disconnection of the medical devices from the patient results in the undesirable disruption of medical monitoring and/or treatment therefor. Hand carrying the medical devices along with the patient requires extra personnel, which may not be available, or for which there may not be adequate room within the transport vehicle.

As such, it is desirable to provide a system for transporting a medical patient wherein the medical devices are carried along with the stretcher. In an attempt to provide such a system for transporting a medical patient while facilitating the continuous use of medical devices thereupon, the Mobile Intensive Care Rescue Facility (MIRF) was developed by the Royal Australian Army Medical Corp. The MIRF is intended to provide sufficient medical equipment to have the capabilities of an intensive care hospital ward. The MIRF is designated so as to facilitate the removal and replacement of the various pieces of medical equipment therefrom for maintenance. The MIRF is specifically designed to accommodate two major roles: the transfer of critically ill people from one point to another, such as from a ward to an x-ray room or from one hospital to another; and the bringing of life support systems quickly to the scene of an accident or other medical emergency.

The MIRF can be configured to include a blood pressure cuff, an invasive blood pressure monitor, a body temperature sensor, a heart rate sensor (finger clip sensor), an oxygen saturation sensor, an exhaled air carbon dioxide sensor, and an electrocardiograph, so as to facilitate medical monitoring of a patient. Further, the MIRF can include a ventilation system, a volumetric infusion pump, a syringe pump, a suction unit, and a defibrillator so as to facilitate medical treatment.

Another contemporary system is the MOBI described in U.S. Pat. No. 4,957,121, issued to Icenogle et al. on Sep. 18, 1990. The MOBI is similar to the MIRF in concept. That is, like the MIRF, the MOBI utilizes off-the-shelf medical devices which are attached to the housing thereof so as to be transportable therewith, thus eliminating disruptions in the medical care provided thereby during transport.

Further examples of such contemporary life support systems include those disclosed in U.S. Pat. Nos. 4,584,989; 4,352,991; 4,691,397; 3,304,116; and 3,341,246.

U.S. Pat. No. 4,584,989 discloses a life support stretcher bed adapted to accommodate patients in intensive or cardiac care units in hospitals. The life support stretcher bed is broadly adapted for electrical medical devices, medical supplies and features an under carriage including a support structural, wheels, a patient housing with a mattress, an electrical power source and supports for mounting the medical equipment.

U.S. Pat. No. 4,352,991 teaches a life support system adapted for field use in a vehicle with available power and includes electrically operable life support units, means for supporting the life support units, a patient stretcher, and a DC power source adapted for battery or remote power source.

U.S. Pat. No. 4,691,397 teaches a device for carrying the life supporting devices of a bedridden patient including a table like means for supporting the devices, an IV holder, wheeled transport means and a hospital bed footboard securing means.

U.S. Pat. No. 3,341,246 teaches a hospital stretcher adapted broadly with a litter structure having telescopic post elements and other means for manipulating the patient to various positions.

As those skilled in the art will appreciate, it would further be desirable to monitor the operation of each of the medical devices and to store or log the results of such monitoring so as to provide both medical and maintenance personnel with useful information. Medical personnel could use the results of such data logging for determining the condition of the patient as well as the treatment which has already been provided to the patient. Maintenance personnel could use such data logging to determine if the medical devices have been operating properly.

Thus, when the transportable life system arrives at a medical facility, medical personnel could immediately access the data logger to determine the status of the patient. Rapid access to such information would greatly aid in the diagnosis and treatment of the patient. For example, if the patient had an irregular heart beat during transport, then medical personnel would immediately be alerted as to the need to continue with monitoring of the heart beat, as well as to the possible need to treat the irregularity.

Maintenance personnel could review the data log so as to determine if the medical monitoring devices were monitoring the patient properly and if the medical treatment devices were applying treatment to the patient in the desired manner. Further, logged parameters such as the time and service for each medical device would provide maintenance personnel with an easy means for determining when routine maintenance should be performed upon each medical device.

However, when the medical devices have previously been approved by a governmental agency, then it is necessary that such data logging be accomplished without interfering with the operation of the medical devices, so as to attempt to maintain the validity of such prior approval. Thus, any signals associated with the medical devices must be taken in a manner which does not affect the performance of the device.

In view of the foregoing, it is desirable to provide a means for logging data provided by medical devices, i.e., medical monitoring devices and medical treatment devices, of a transportable life support system in a manner which does not invalidate prior governmental approval of the medical devices.

SUMMARY OF THE INVENTION

The present invention specifically addresses and alleviates the above mentioned deficiencies associated with the prior art. More particularly, the present invention comprises a method and apparatus for storing information representative of the operation of medical devices in a manner which does not substantially affect operation of the medical devices so that prior governmental approval of the medical devices is more likely to be maintained. According to the present invention, at least one isolation circuit facilitates communication from each of a plurality of separate medical devices to at least one storage device. The isolation circuits are configured so as to mitigate interference with the medical devices, thereby facilitating logging of the communicated data without adversely affecting operation of the medical devices.

According to the preferred embodiment of the present invention, the isolation circuits may comprise either an optical isolator or an output port. Those skilled in the art will appreciate that various other isolation devices or circuits are likewise be suitable.

According to the preferred embodiment of the present invention, optical isolators are used to communicate discrete parameters from the medical devices to the storage device. As defined herein discrete parameters include signals such as those representing the application of power to the medical device.

As those skilled in the art will appreciate, optical isolators limit the amount of signal which is removed or modified from the light transmitting side of the circuit, i.e., that side of the circuit which is being sensed, and also prevent the introduction of stray or undesirable signals from the light receiving side of the circuit. Thus, the use of such optical isolators substantially limits the effect of such monitoring upon the monitored circuitry.

Similarly, built-in output ports of the medical devices, such as RS-232 ports, are utilized to provide isolation of the medical devices from the storage device while communicating logic signals from the medical devices to the storage device. As defined herein, logic signals include those representative of the functioning of the medical devices, such as signals representative of the monitored condition of the patient as provided by medical monitoring devices and the therapy provided to the patient by medical treatment devices. It is understood that the distinction between discrete parameters and logic signals is not always clear and that either type of signal may be isolated in either manner, as desired. In some instances, as discussed in further detail below, it may even be desirable to provide both types of isolation, i.e., optical isolation and the use of an output port, so as to better assure complete electrical isolation of a medical device and/or so as to prevent electrical problems which may occur when a common ground is utilized for the medical deice and the transportable life support system.

Thus, according to the methodology of the present invention, data logging is preformed by providing a first signal representative of a state of a discrete parameter of a medical device to a storage device. The step of providing a first signal representative of a state of a discrete parameter of a medical device to a storage device comprises the steps of: providing the discrete parameter to an optical isolator so as to cause the optical isolator to define the first signal; and communicating the first signal to the storage device. A second signal representative of at least one logic output of the medical device is also provided. The step of providing the second signal representative of at least one logic output of the medical device comprises the steps of: providing the logic signal to an output port of the medical device so as to cause the output port to define the second signal; and communicating the second signal to the storage device. The first and second signals are stored in the storage device.

For example, the step of providing at least one first signal representative of a state of a discrete parameter comprises providing at least one first signal representative of an application of power to a medical device.

According to the preferred embodiment of the present invention, the step of providing the logic signal to an output port comprises providing the output signal to an RS-232 port.

According to the present invention, the medical devices are monitored, but control of the medical devices remains unaltered. That is, the devices are controlled individually, in the same manner as when submitted for governmental approval. No centralized computer control is provided.

These, as well as other advantages of the present invention will be more apparent from the following description and drawings. It is understood that changes in the specific structure shown and described may be made within the scope of the claims without departing from the spirit of the invention.

Thus, according to the preferred embodiment of the present invention, a transportable life support system comprises a data logger for providing information regarding the condition of the patient and the operation of the medical devices thereof.

DETAILED DESCRIPTION OF THE PREFERRED INVENTION

The detailed description set forth below in connection with the appended drawings is intended as a description of the presently preferred embodiment of the invention, and is not intended to represent the only form in which the present invention may be constructed or utilized. The description sets forth the functions and the sequence of steps for constructing and operating the invention in connection with the illustrated embodiment. It is to be understood, however, that the same or equivalent functions may be accomplished by different embodiments that are also intended to be encompassed within the spirit and scope of the invention.

The data logger for transportable life support system of the present invention is illustrated in FIGS. 1 through 4 which depict a presently preferred embodiment thereof.

Figure 1:
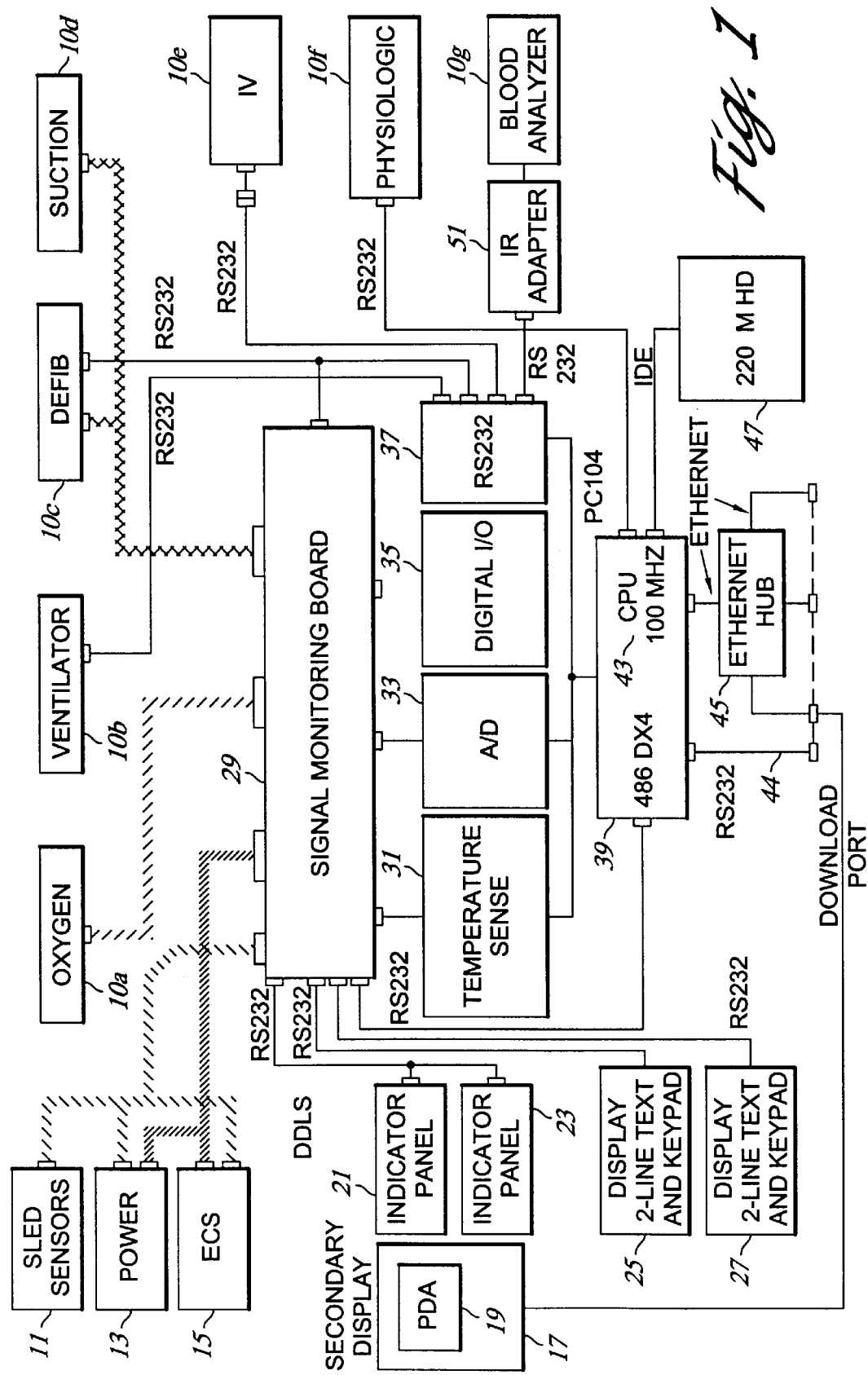
FIG. 1 is a block diagram showing the interconnection of exemplary medical devices, i.e., medical monitoring devices and medical treatment devices, with data logging or storage devices in a manner which does not adversely affect the operation of the medical devices.

Referring now to FIG. 1, a plurality of medical devices 10a–10g, including both medical monitoring devices and medical treatment devices, are in electrical communication with hard disk or storage device 47 of a data logging system such that the operation of the medical devices 10a–10g may be monitored and desired parameters from the medical devices 10–10g stored within the storage device 47 for subsequent retrieval. As discussed in detail above, such retrieval of the operational parameters associated with the medical devices 10a–10g facilitates both enhanced patient care and enhanced maintenance of the medical devices 10a–10g.

According to the preferred embodiment of the present invention, discrete parameters associated with the medical devices 10a–10g are monitored via optical isolators (105 of FIG. 2, for example) and logical outputs of the medical devices 10a–10g are monitored via built-in RS-232 port of the medical device's 10b–10g themselves. In this manner, critical parameters associated with the medical devices 10a–10g are monitored and logged without interfering with the proper operation of the medical devices 10a–10g and also potentially without invalidating prior governmental approval of the medical devices 10a–10g. Each medical device 10a–10g may utilize either an optical isolator or a built-in RS-232 port, or a combination of both, as desired.

According to the preferred embodiment of the present invention medical devices 10a–10g such as oxygen 10a and ventilator 10b provide their discrete parameters to the storage device 47 via signal monitoring board 29 which provides an electrical interface therefore. The signal monitoring board 29 provides signal conditioning for the discrete parameters and also may facilitate additional functionality, such as the triggering of audible alarms when such discrete parameters indicate an undesirable condition of the medical devices 10a–10g. According to the preferred embodiment of the present invention, a 100 MHz 486 PC single board system is utilized to control the system. The board 39 preferably incorporates several expansion board equivalents, including video processing, IEEE 802.3 Ethernet and SCSI Interfaces, IDE Controller, and serial port interfaces, which are included on a single board, low powered, 8.0×5.75 inch footprint. The board 39 preferably uses the PC-104 expansion bus standard to add hardware modules for functional expansion.

Four PC-104 interface modules are incorporated into the design to allow the data logger to communicate with the medical devices. According to the preferred embodiment of the present invention, a custom-printed signal monitoring board is utilized to provide signal conditioning and interfacing between the AMPRO board 39 and the medical devices 10a–10g, according to well known principles.

According to the preferred embodiment of the present invention, with the help of the interface capability of the signal monitoring board 29, the system facilitates the acquisition of information from up to 8 RS-232 serial ports, 64 digital ports, 35 analog ports, and 8 temperature ports. Data from all of these interfaces may be acquired and processed by the AMPRO CPU 43 and then stored on the 220 MByte ruggedized hard drive 47. As those skilled in the art will appreciate, various other means for storing the acquired data may be utilized.

Further, according to the preferred embodiment of the present invention the data logging system comprises an Ethernet interface to facilitate remote connections, efficient downloading of the log data, and real time display of selected information to secondary display units 17, such as a Personal Digital Assistant 19.

The Ethernet interface 45 allows a logistics operator to perform maintenance activities on the embedded device or to network a number of such transportable life support systems to a single nurses station.

According to the preferred embodiment of the present invention, the data logging system is activated any time that power is turned on for the transportable life support system. Thus, no special action is required of an operator in order to initiate continuous data logging.

Oxygen sensor 10a facilitates monitoring of the level of remaining oxygen in the on-board oxygen tank. Ventilator 10b assists the patient in breathing. Defibrillator 10c provides defibrillation to the patient's heart, as needed. Suction 10d is utilized to remove undesirable fluid from the patient (from the patient's lungs or a wound, for example). IV 10e provides for the infusion of fluids into the patient. Physiological monitoring 10f facilitates the monitoring of various physiological parameters according to well known principles. Blood analyzer 10g analyzes desired parameters of the patient's blood.

Sled sensors 11 monitor various aspects of the transportable life support system, such as the temperature of critical components thereof. Power 13 provides power to the electrical components of the transportable life support system. The Environmental Control System (ECS) 15 provides heating and/or cooling to the various devices of the transportable life support system, as required.

The secondary display 17 preferably comprises a personal digital assistant (PDA) 19 which is optionally used to monitor the status of the patient and transportable life support system.

A Display and Data Logging System (DDLS) comprises an indicator panels 21 and 23 which provides indications representative of the operation of the medical monitoring and medical treatment devices. Display 2-line text and keypads 25 and 27 facilitate data entry for obtaining status of the medical monitoring and treatment devices.

According to the preferred embodiment of the present invention, the signal monitoring board 29 provides an interface for the medical monitoring and treatment devices and the controls and displays therefore, according to well known principles. Temperature sensing system 31 facilitates the sensing of temperatures at various locations of the transportable life support system. A/D converter 33 facilitates interface of the signal monitoring board 29 with CPU 43. It is important to note that the CPU board 39 do not function to control any medical treatment devices. Indeed, none of the medical treatment devices of the present invention are controlled by a CPU which is not a part of the device itself. That is, the medical treatment devices of the present invention are not under common control.

Similarly, digital I/O 35 facilitates interface of the signal monitoring board 29 with CPU 43. RS-232 interface facilitates interface of the ventilator 10b, the defibrillator 10c, IV 10e, and blood analyzer 10g, with the CPU 43.

CPU 43 preferably comprises a 486 DX4 41 driven by a 100 MHZ clock.

According to the preferred embodiment of the present invention, an RS-232 port 44 and an Ethernet hub 45 facilitate communication between the transportable life support system and other devices, such as computers, communications equipment, and other transportable life support systems. The secondary display 17 is preferably interfaced with the transportable life support system via Ethernet hub 45. However, those skilled in the art will appreciate that the secondary display 17 may be interfaced with the transportable life support system via various different means.

The storage device of the present invention preferably comprise one 220 MByte hard drive 47 which is in electrical communication with the CPU 43.

According to the preferred embodiment of the present invention, the blood analyzer 10g communicates via infrared (IR) adaptor 51. The IR adaptor 51 comprises an RS-232 port to facilitate communications with the RS-232 interface 37.

Figure 2:
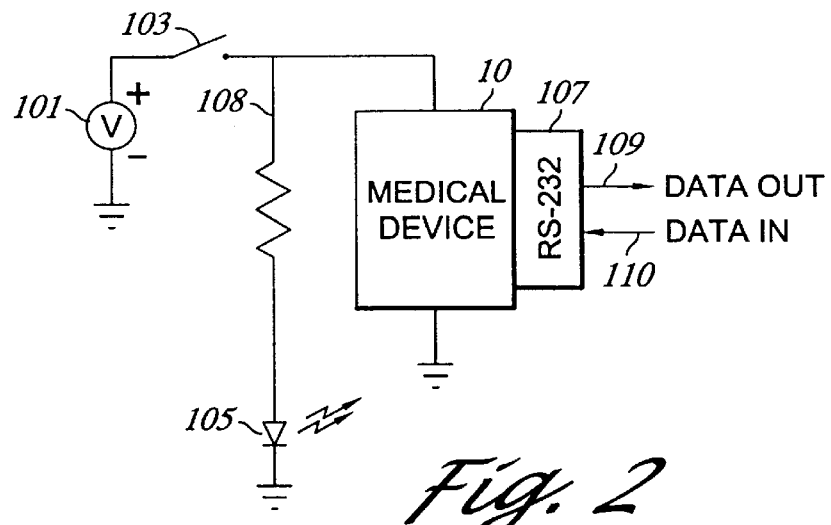
FIG. 2 is an electrical schematic showing the interface of an exemplary medical device to a data logger.

Referring now to FIG. 2, the present invention generally comprises a data logger for receiving information from a medical device 10 in a manner which potentially does not invalidate prior governmental approval of the medical device 10. Note that the medical device 10 is a generic reference to any of the medical devices 10a–10g of FIG. 1. Thus, any of the medical devices 10a–10g may be interconnected to the data logger via either an optical isolator 105 or a built in RS-232 port 107 (or a similar built in output port) as desired an/or as dictated by the medical device (as determined by whether or not the medical device is provided with a built-in RS-232 output port).

The present invention comprises an interface to the medical device 10 which facilitates monitoring of the medical device 10 in a manner which does not adversely affect the operation thereof. According to the preferred embodiment of the present invention, the interface comprises an optical isolator 105 which provides a signal representative of the status of the application of a discrete or power signal to the medical device 10. Thus, when power is applied from power source 101 via switch 103 to medical device 10, then optical isolator 105 provides a signal to the data logger or storage device 47 of FIG. 1. Resistor 108 defines the working current of optical isolator 105.

Optionally, the medical device 10 further comprises an RS-232 port 107 which provides at least one output 109 and optionally one or more inputs 110. Each output 109 of RS-232 port 107 provides a data channel for logical signals, such as those representative of medical treatment provided by medical treatment devices and measure parameters measured by medical monitoring devices.

Figure 3:
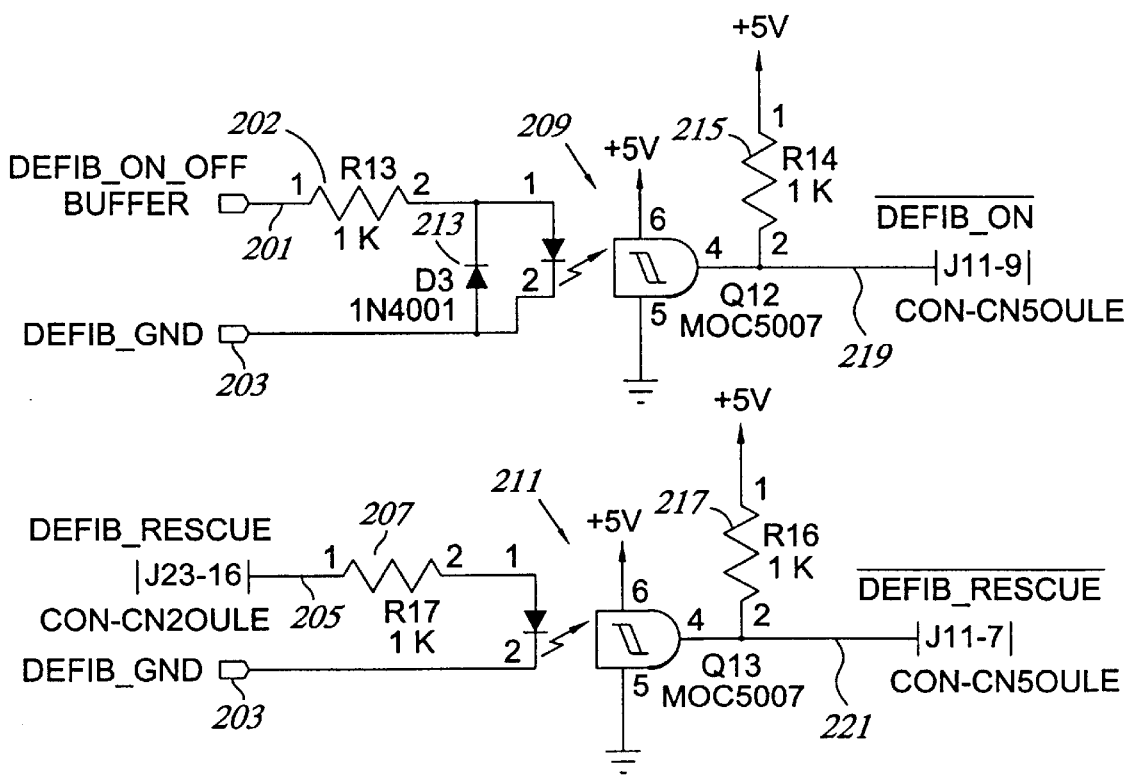
FIG. 3 is a schematic showing the interconnection of a medical device to a data logger in further detail.

Referring now to FIG. 3, an example of the use of optical isolators 209, 211 for a particular medical device, i.e., the defibrillator, is shown. In this example two discrete parameters are monitored. DEFIB-ON-OFF-BUFFER is a signal which indicates whether or not the defibrillator has power applied thereto. According to the preferred embodiment of the present invention, the application power to the defibrillator results in the application of power to optical isolator 209. Current limiting resistor 202 regulates the amount of current which flows through optical isolator 209 and protection diode 213 provides over-voltage protection therefor. The output of optical isolator 209 is representative of the status of the application of power to the defibrillator. Thus, when power is not applied to the defibrillator, then no current flows through optical isolator 209 and no output signal is provided therefrom, thus allowing the output thereof to be pulled positive through resistor 215. The application of power to the defibrillator causes the output of the optical isolator 209 to be pulled to ground. Those skilled in the art will appreciate that various other configurations of the optical isolator 209 are likewise suitable.

The second discrete parameter associated with the defibrillator is the DEFIB-RESCUE signal which is representative of the system readiness for application of defibrillation current to the patient. The DEFIB-RESCUE circuit is similar to the DEFIB-ON-OFF-BUFFER circuit with the exception that an over compensation diode is not required since the power level is lower. Thus, the application of a DEFIB-RESCUE signal to the input 205 of the circuit causes current to pass through resistor 207 to ground 203, thereby actuating optical isolator 211. As in the DEFIB-ON-OFF-BUFFER described above, plus 5 volts sensed at output 221 via resistor 217 until the optical isolator 211 is actuated. The optical isolator 211 then pulls output 221 to ground, thereby indicating the system readiness for application of defibrillation current to the patient.

Figure 4:
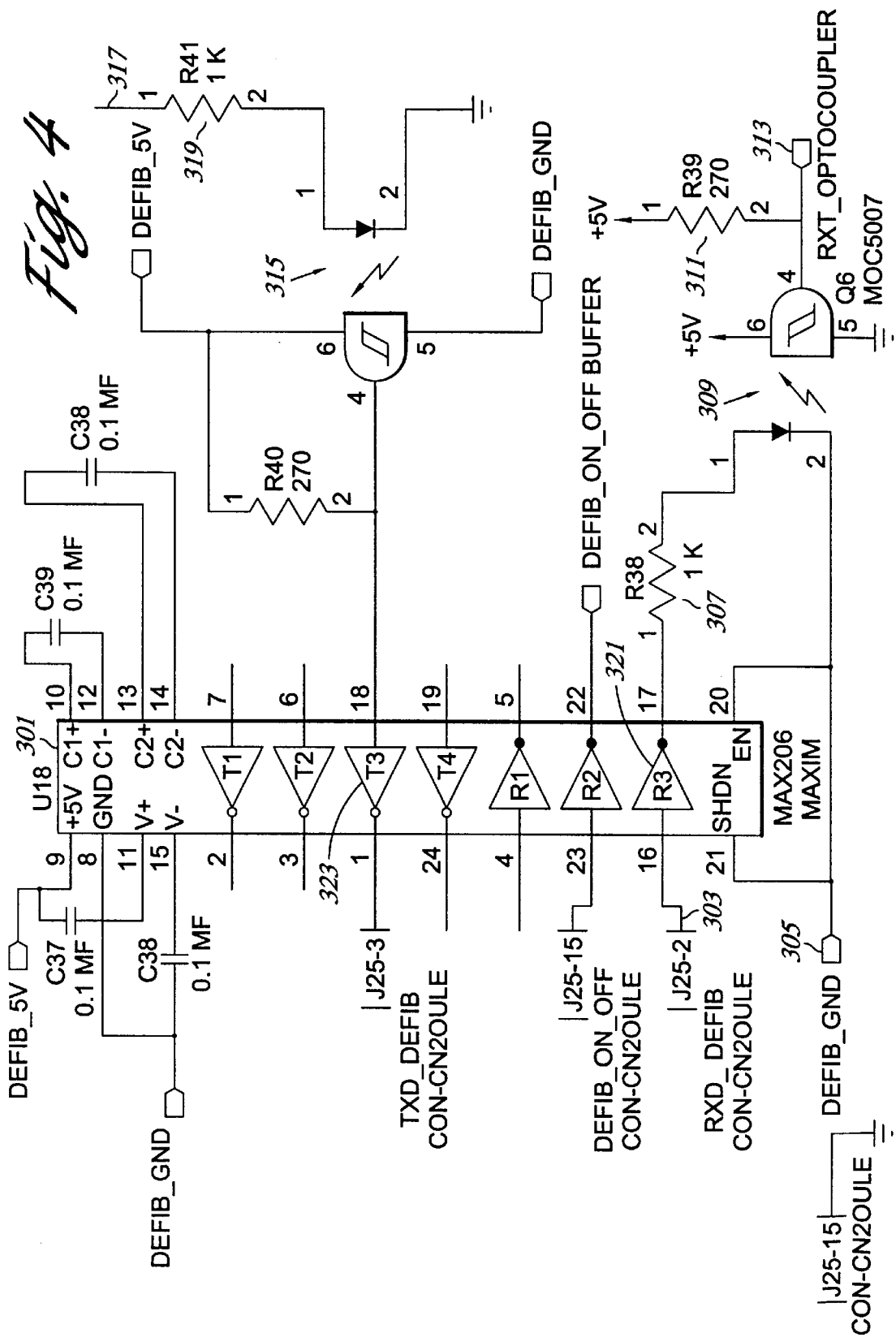
FIG. 4 is a schematic showing the interconnection of a medical device to a data logger in further detail.

Referring now to FIG. 4, the RS-232 translator IC chip 301 for providing logic signals from a medical device to the storage device 47 is shown. The RS-232 port comprises individual RS-232 to TTL-level translators 323, 321 which assist in buffering and isolation of signals transmitted to and from the RS-232 port so as to mitigate undesirable interference with the medical device.

The RXD-DEFIB signal, which is the RS-232 logic signal from the defibrillation unit indicating the status of the defibrillator, is thus isolated from the data logger via translator 321 of the RS 232 chip 301.

According to the preferred embodiment of the present invention, the defibrillator is completely electrically isolated from the data logger, thus necessitating the further use of optical isolators 309 and 315. This is due to the extremely high voltage as generated by the defibrillator. Other medical devices do not generally require such additional isolation. Thus, according to the preferred embodiment of the present invention, the RDX-DEFIB signal is isolated or buffered by both the RS-232 output chip 301 and optical isolator 309. The output 313 of the optical isolator 309 is thus electrically isolated from the defibrillator. A logical input 317 TXD-DEFIB to the defibrillator is provided through resistor 319 to optical isolator 315 and translator 323 of RS-232 chip 301 in a similar fashion. In this manner, both logical inputs and outputs to the defibrillator 10c are completely electrically isolated from the remainder of the transportable life support system.

Thus, according to the present invention, both discrete parameters and logic signals associated with medical devices 10 are monitored and stored in a manner which does not adversely affect operation of the medical device 10 and thus potentially does not invalidate prior governmental approval thereof.

Figure 5:
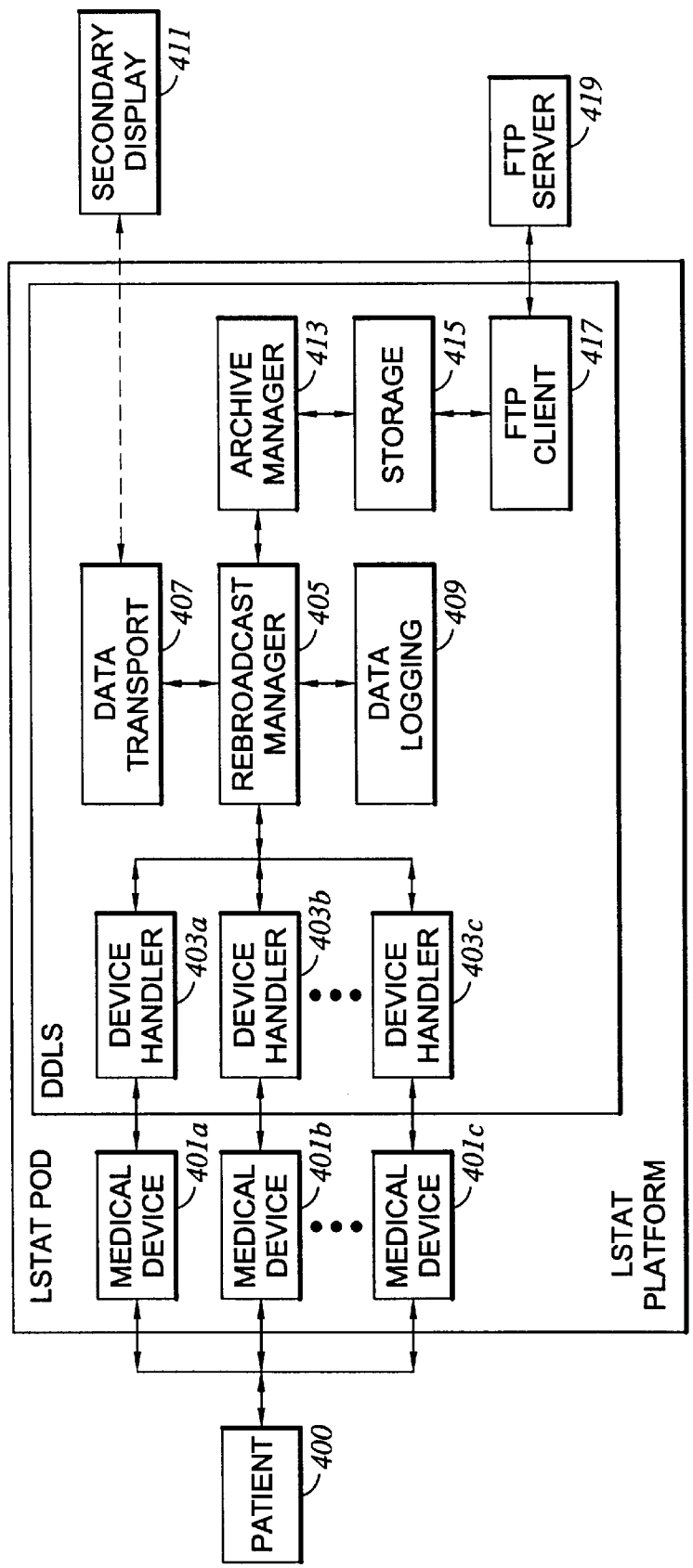
FIG. 5 is a block diagram illustrating the process overview of the invention.

Referring now to FIG. 5, a block diagram illustrating the process overview of the invention, is shown therein. The process of the present invention begins with the medical devices and ends with logged in display data. The existing medical devices 401a, 401b, 401c that operatively monitor patient 400, gathering and processing medical data normally. Instrumentation and data monitors interface with the medical devices to extract that data nonintrusively, by using software and hardware techniques. This minimal impact to the medical devices is important because it allows the invention to leverage existing Food and Drug Administration (FDA) pedigree of the medical devices. The medical devices 401a, 401b, 401c communicate information to the device handlers 403a, 403b, 403c. The device handlers, using a common time base, timestamp the data from the time the medical devices deliver the data to the rebroadcast manager 405, a central distribution point. The common timestamps provide the basis for synchronization of the data for later clinical analysis. This is important because new treatment algorithms can be created from this data into the common time base line.

The rebroadcast manager 405 then relays the data to the data transport device 407, archive manager 413, and data logging device 409. The central distribution point of rebroadcast manager 405 is further important because it ensures that the data being displayed and the data being logged are identical. The data transport device 407 communicates the data to secondary display 411. The secondary display then collects the received data into a coherent format. The data archive manager 413 provides a caching of data for quick retrieval by the secondary display. The archive manager 413 implements a virtual medical device that records important data—for instance, to implement a trending display of medical parameters. Consequently, data can be broken down and recombined in various and differing ways. The data logger 409 records data in secondary storage device 415 for later retrieval. The secondary storage device 415 can be accessed via FTP client 417 and FTP server 419.

It is understood that the exemplary data logger for a transportable life support system described herein and shown in the drawings represents only a presently preferred embodiment of the invention. Indeed, various modifications and additions may be made to such embodiment without departing from the spirit and scope of the invention, for example, those skilled in the art will appreciate that various isolation means are equivalent to the use of an optical isolator. For example, an acoustic isolator or a mechanical isolator may similarly be utilized. Further, various types of output ports may be utilized in place of an RS-232 port and thus are considered equivalent to an RS-232 port and may be used instead. Thus, these and other modifications and additions may be obvious to those skilled in the art may be implemented to adapt the present invention for use in a variety of different applications.

What is claimed is:

1. A method for logging information representative of operation of medical devices, the method comprising the steps of:
    a) providing a storage device for logging information representative of operation of medical devices; and
    b) communicating information from a plurality of medical devices to the storage device via at least one isolation circuit, the isolation circuit(s) mitigating interference with the medical devices so as to facilitate logging without adversely affecting operation of the medical devices.

2. The method as recited in claim 1, wherein the step of communicating information from a plurality of medical devices to the storage device via at least one isolation circuit comprises communicating information from a plurality of medical devices to the storage device via at least one of an optical isolator and an output port.

3. The method as recited in claim 1, wherein the step of communicating information from a plurality of medical devices comprises communicating information from a plurality of medical devices disposed upon a transportable life support system.

4. A method for logging information representative of operation of medical devices, the method comprising the steps of:
    a) providing a first signal representative of a state of a discrete parameter of a medical device to a storage device, the step of providing a first signal representative of a state of a discrete parameter of a medical device to a storage device comprising the steps of:
        i) providing the discrete parameter to an optical isolator so as to cause the optical isolator to define the first signal;
        ii) communicating the first signal to the storage device;
    b) providing a second signal representative of at least one logic output of the medical device, the step of providing a second signal representative of at least one logic output of the medical device comprising the steps of:
        i) providing the logic signal to an output port of the medical device so as to cause the output port to define the second signal;
        ii) communicating the second signal to the storage device; and
    c) storing the first and second signals in the storage device;
    d) wherein the steps of providing the discrete parameter to an optical isolator and providing the logic signal to an output port facilitate monitoring of the medical devices in a manner which mitigates interference with operation of the medical devices so as to maintain a reliability and effectiveness thereof.

5. The method as recited in claim 4 wherein the step of providing at least one first signal representative of a state of a discrete parameter comprises providing at least one first signal representative of an application of power to a medical device.

6. The method as recited in claim 4, wherein the step of providing the logic signal to an output port comprises providing the output signal to an RS-232 port.

7. The method as recited in claim 4, wherein the step of providing a second signal further comprises the steps of providing an output of the output port to an optical isolator so as to define the second signal.

8. A data logger for storing information representative of operation of medical devices, the data logger comprising:
    a) a storage device for storing information representative of operation of medical devices; and
    b) at least one isolation circuit for communicating information from a plurality of medical devices to the storage device, the isolation circuit(s) configured to mitigate interference with the medical devices so as to facilitate logging without adversely affecting operation of the medical devices.

9. The data logger as recited in claim 8, wherein the isolation circuit(s) comprise at least one of an optical isolator and an output port.

10. The data logger as recited in claim 8, wherein the medical devices are disposed upon a transportable life support system.

11. A data logger for storing information representative of operation of medical devices, the data logger comprising:

a) a first circuit for providing to a storage device a first signal representative of a state of a discrete parameter of a medical device, the first circuit comprising a first optical isolator and;

b) a second circuit for providing to the storage device a second signal representative of at least one logic output of the medical device, the second circuit comprising an output port of the medical device;

c) wherein providing the discrete parameter to an optical isolator and providing the logic signal to an output port facilitate monitoring of the medical devices in a manner which mitigates interference with operation of the medical devices so as to maintain a reliability and effectiveness thereof.

12. The data logger as recited in claim 11, wherein the first circuit is configured to provide a first signal representative of an application of power to a medical device.

13. The data logger as recited in claim 11, wherein the second circuit comprises an RS-232 port.

14. The data logger as recited in claim 11, wherein the second circuit is configured to provide an output of the output port to an optical isolator so as to define the second signal.

\* \* \* \* \*